United States Patent
Lomans

(10) Patent No.: US 10,391,419 B1
(45) Date of Patent: Aug. 27, 2019

(54) ISOLATION AND PURIFICATION OF CONJUGATED ESTROGENS

(71) Applicant: NOSTRUM PHARMACEUTICALS. LLC., Somerset, NJ (US)

(72) Inventor: John S. Lomans, Middleburgh, NY (US)

(73) Assignee: NOSTRUM PHARMACEUTICALS. LLC., Somerset, NJ (US)

(*) Notice: Subject to any disclaimer, the term of this patent is extended or adjusted under 35 U.S.C. 154(b) by 46 days.

(21) Appl. No.: 15/042,676

(22) Filed: Feb. 12, 2016

Related U.S. Application Data

(60) Provisional application No. 62/115,451, filed on Feb. 12, 2015.

(51) Int. Cl.
| | |
|---|---|
| *A61K 31/565* | (2006.01) |
| *A61K 31/566* | (2006.01) |
| *B01D 11/02* | (2006.01) |
| *B01D 61/58* | (2006.01) |
| *B01D 61/14* | (2006.01) |

(52) U.S. Cl.
CPC ........ *B01D 11/0203* (2013.01); *A61K 31/565* (2013.01); *A61K 31/566* (2013.01); *B01D 11/0207* (2013.01); *B01D 61/145* (2013.01); *B01D 61/147* (2013.01); *B01D 61/58* (2013.01)

(58) Field of Classification Search
CPC ................ A61K 31/565; A61K 31/566; B01D 11/0203; B01D 61/145; B01D 61/58; B01D 61/147
See application file for complete search history.

(56) References Cited

U.S. PATENT DOCUMENTS

| | | |
|---|---|---|
| 2,696,265 A | 12/1954 | Beall et al. |
| 2,711,988 A | 6/1955 | Deaus |
| 2,834,712 A * | 5/1958 | Beail ............... A61K 38/24 424/546 |
| 5,723,454 A | 3/1998 | Ban et al. |
| 5,855,704 A | 1/1999 | Reuter |
| 7,081,451 B2 | 7/2006 | Ahnsorge et al. |
| 7,964,586 B2 | 6/2011 | Rasche et al. |
| 8,349,819 B2 * | 1/2013 | Lomans .............. C07J 1/00 424/545 |
| 10,143,938 B2 | 12/2018 | Kkula et al. |
| 2014/0371180 A1 | 12/2014 | Akula et al. |

OTHER PUBLICATIONS

Kureckova et al., "Supercritical fluid extraction of steroids from biological samples and first experience with solid-phase microextraction-liquid chromatography." J. Chromatography B, vol. 770, pp. 83-89, 2002.*

Patel et al., "Evolution of strategies to achieve baseline separation of ten anionic, water-soluble sulfated estrogens via achiral packed column supercritical fluid chromatography." J. Chromatography A, vol. 1370, pp. 240-245 (Year: 2014).*

Hyatt, "Liquid and Supercritical Carbon Dioxide as Organic Solvents," J. Org. Chem., 1984, 49, 5097-5101.

* cited by examiner

*Primary Examiner* — Barbara P Badio

(74) *Attorney, Agent, or Firm* — Scully Scott Murphy and Presser; Tanzina Chowdhury

(57) ABSTRACT

A method of obtaining conjugated estrogens from pregnant mare's urine by supercritical fluid extraction and the product thus obtained is disclosed.

17 Claims, 1 Drawing Sheet

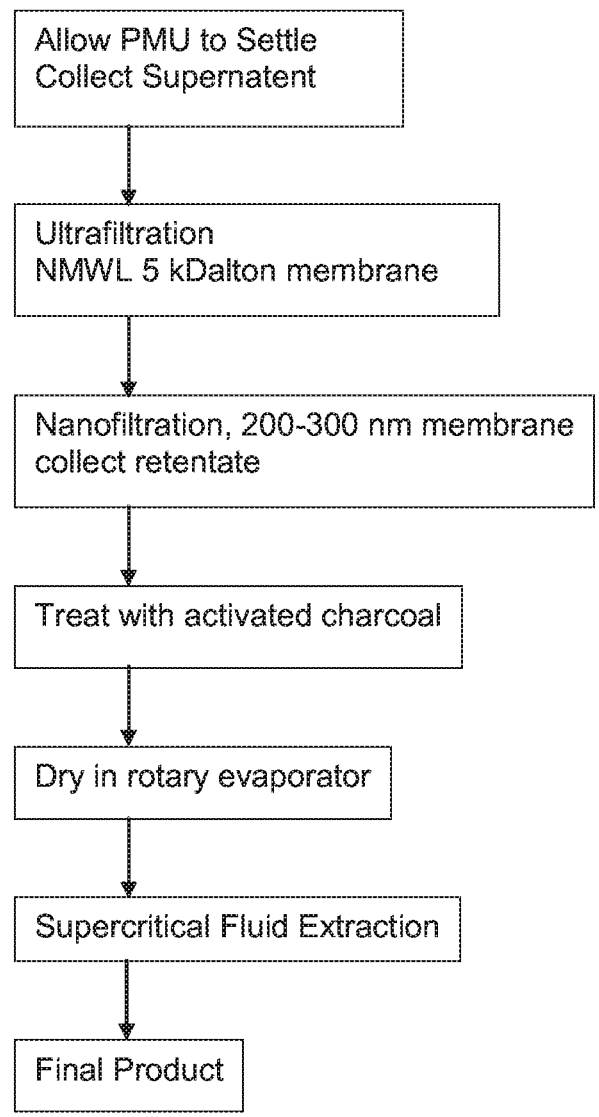

ISOLATION AND PURIFICATION OF CONJUGATED ESTROGENS

RELATED APPLICATIONS

This application is claiming priority of provisional application filed on Feb. 12, 2015 and having Ser. No. 62/115,451

FIELD OF THE INVENTION

This invention relates to the isolation of natural products using supercritical fluid extraction.

BACKGROUND

Conjugated estrogens obtained from pregnant mares' urine are a mixture of the sodium salts of 3-sulfated estrogenic substances. These 3-sulfate estrogens are secreted in substantial quantities in the urine of pregnant mares (pregnant mares' urine; PMU). Following this discovery in the 1930's, a pharmaceutical preparation of estrogens obtained from pregnant mares was marketed as a hormone replacement therapy in 1942, as PREMARIN®. PREMARIN® is still on the market today as an important therapeutic agent.

The major estrogenic substances in PREMARIN® are sodium estrone sulfate and sodium equilin sulfate. Also present are sodium sulfate conjugates of 17α-dihydroequilin, 17α-estradiol, and 17β-dihydroequilin. Tablets for oral administration are available in 0.3 mg, 0.45 mg, 0.625 mg, 0.9 mg, and 1.25 mg strengths of conjugated estrogens. PREMARIN® is also available as a cream.

Pharmaceutical preparations of conjugated estrogens are used to treat symptoms of menopause and other conditions as a form of hormone replacement therapy. Menopause is generally defined as the last natural menstrual period of a woman and is characterized by the cessation of ovarian function, leading to the substantial diminution of circulating estrogen in the bloodstream. Menopause is usually identified, in retrospect, after 12 months of amenorrhea. It is not a sudden event, but is often preceded by a time of irregular menstrual cycles prior to eventual cessation of menses. Following the cessation of menstruation the decline in endogenous estrogen concentrations is typically rapid. There is a decrease in serum estrogens from circulating levels ranging from 40-250 pg/mL of estradiol and 40-170 pg/ml of estrone during ovulatory cycles to less than 15 pg/mL of estradiol and 30 pg/mL of estrone in postmenopausal women.

As these estrogens decline during the time preceding (perimenopuase) and following the menopause (postmenopause), various physiological changes may result, including vulvar and vaginal atrophy causing vaginal dryness, pruritus and dysparenuia, and vasomotor instability manifested as hot flushes. Other menopausal disturbance may include depression, insomnia, and nervousness. The long-term physiologic effects of postmenopausal estrogen deprivation may result in significant morbidity and mortality due to increase in the risk factors for cardiovascular disease and osteoporosis. Menopausal changes in blood lipid levels, a major component of the pathogenesis of coronary heart disease (CHD), may be precursors to increased incidence of ischemic heart disease, atherosclerosis, and other cardiovascular disease. A rapid decrease in bone mass of both cortical (spine) and trabecular (hip) bone can be seen immediately after the menopause, with a total bone mass loss of 1% to 5% per year, continuing for 10 to 15 years.

Hormone replacement therapy (HRT) using estrogens is beneficial for symptomatic relief of hot flushes and genital atrophy associated menopause and is useful for prevention of postmenopausal osteoporosis. HRT has been recognized as an advantageous treatment for relief of vasomotor symptoms. There is no acceptable alternative to estrogen treatment for the atrophic changes in the vagina; estrogen therapy increases the vaginal mucosa and decreases vaginal dryness. Long term HRT is also used to prevent osteoporosis because estrogen therapy can decrease bone loss, reduce spine and hip fracture, and prevent loss of height. In addition, HRT has been shown to be effective in increasing high density Lipoprotein-cholesterol (HDL-C) and in reducing low density lipoprotein cholesterol (LDL-C), affording possible protection against CHD. HRT also can provide antioxidant protection against free radical mediated disorders or disease states. Estrogens have also been reported to confer neuroprotection, and inhibit neurodegenerative disorders, such as Alzheimer's disease. PREMARIN® is a popular HRT available worldwide, and is believed to be an effective treatment for all of these disorders.

Natural mixtures of conjugated estrogens such as found in the urine of pregnant mares have proved particularly effective and well tolerated for HRT. The dissolved solids content in PMU may naturally vary within wide ranges, and may generally lie in a range of 40-90 g dry matter per liter. In addition to urea and other usual urine contents, phenolic constituents are contained in the solids content of the PMU in quantities of about 2%-5% by weight related to dry matter. These phenolic constituents include cresols and dihydro-3,4-bis[3-hydroxyphenyl)methyl]-2(3H)-furanone (HPMF). These phenolics may be present in free or conjugated form. The PMU contains a natural mixture of estrogens which is largely present in conjugated form, e.g. as sulfuric acid semi-ester sodium salt (referred to hereinafter as "sulfate salt"). The content of conjugated estrogens (calculated as estrogen sulfate salt) may be between 0.3% and 1% by weight relative to dry matter.

Conventionally, conjugated estrogens are obtained from PMU by various drying, trituration, and liquid-liquid extraction methods. Conjugated estrogens have been obtained by extraction with a polar organic solvent which is immiscible with water, or only slightly miscible, such as ethyl acetate, n-butanol or cyclohexanol. In such liquid-liquid extractions, however, a number of problems occur, such as foaming, sedimentation, emulsification and poor phase separation. Generally several extraction steps are required, which results in losses and only partial recovery of the estrogen content. Conjugated estrogens have also been isolated by extracting PMU and an organic solvent such as n-butanol or instead by adsorption on charcoal. Such methods have involved a multiplicity of individual process operations, involving back extraction and repeated transfer between n-butanol and aqueous solutions. Such repeated extractions generally result in losses of conjugated estrogens and thus only partial recovery of the estrogen content of the PMU. Examples of extraction process are disclosed in U.S. Pat. Nos. 2,696,265; 2,711,988 and 2,834,712.

Several newer purification methods have been developed, for example employing non-ionic resin adsorption, for example as disclosed in U.S. Pat. No. 7,964,586 and U.S. Pat. No. 5,723,454, and ion exchange resins, for example as disclosed in U.S. Pat. No. 6,855,704 and U.S. Pat. No. 7,081,451.

The isolation process for obtaining purified conjugated estrogens from PMU must preserve the estrogenic sulfate group and remove non-sulfated estrogenic components.

Prior art processes for the purification result in solids suitable for pharmaceutical use containing about 25% of conjugated estrogens. The exact quantity of conjugated estrogens must be assayed, since the quantity of conjugated estrogens in pharmaceutical preparations is based on the actual assay.

Furthermore, non-sulfated "non-conjugated" components are undesirable impurities in conjugated estrogen mixtures. The USP monograph for conjugated estrogens specifies that the limit of free steroid impurities should not exceed 1.3%.

BRIEF SUMMARY

The instant invention provides a process for preparing purified conjugated estrogens comprising subjecting said mass of pregnant's mare urine which has been dried to a moisture content of less than about 2% (w/w) to supercritical fluid extraction ("SFE") in a supercritical fluid extraction vessel using supercritical carbon dioxide as the fluid phase to remove impurities present therein and isolating purified conjugated estrogens therefrom. In one embodiment, the SFE step elutes non-polar (lipophilic) impurities, leaving purified conjugated estrogens suitable for pharmaceutical use. In an optional embodiment, a second SFE step is performed by adding water to the supercritical carbon dioxide in the supercritical fluid extraction vessel in an amount sufficient to provide a pH ranging from about 4 to about 6; but the amount of water added is sufficiently small so that the contents of the supercritical fluid extraction vessel has less than 3% (w/w) moisture content. This water addition is followed by the addition of non-polar and/or water immiscible solvent so that the mixture of supercritical carbon dioxide, water and non-polar or water immiscible solvent is the extracting media, wherein the non-polar or water immiscible solvent added ranges from about 0.10% to about 25% (v/v) of the solid and liquid material in the supercritical fluid extraction vessel.

Examples of non-polar and/or water immiscible solvents include alkanes having 1 to 10 carbon atoms, aromatic compounds containing a benzene ring which may be optionally substituted with 1 or two carbon atoms, or an ether of the formula R1OR2, wherein R1 and R2 are independently alkane having 1 to 4 carbon atoms or R1 and R2 taken together with the oxygen atom to which they are attached form a 5- or 6-membered saturated ring containing one oxygen ring atom and the remaining ring atoms are carbon atoms, i.e., the ring contains no carbon-carbon double or triple bonds. Useful non-polar and/or water immiscible solvents include methane, propane, hexane, benzene, and tetrabutylmethyl ether and the like. In the second SFE, the mixture of the liquid carbon dioxide and the non-polar and/or water immiscible solvent elute lipophilic impurities more efficiently.

BRIEF DESCRIPTION OF THE DRAWING

These and other features, aspects, and advantages of the present invention will become better understood with regard to the following description, appended claims, and accompanying drawings (some of the drawings may be not drawn to scale and some of the drawings may be drawn at the indicated scale; further, where scale and/or dimensions are provided, they are provided as examples only) wherein:

FIG. 1 shows a flow chart of a process for obtaining conjugated estrogen starting from dried PMU.

DETAILED DESCRIPTION

As indicated hereinabove, the present application describes a new process for obtaining conjugated estrogens and to the product obtained thereby. The conjugated estrogens are prepared from pregnant mare's urine. In one embodiment, the pregnant mare's urine has been dried. By dried, as used herein, it is meant that the moisture content is about 2% (w/w) or less. The pregnant mare's urine can be dried by any technique known in the art, such as for example, spray dried.

In another embodiment, the pregnant mare's urine may have been processed. By "processed", as used herein, denotes that the PMU has been subjected to one or more separation processes known in the art, including, but not limited to, liquid-liquid extractions, non-ionic resin adsorption, ion exchange chromatography, and the like, and then separating and collecting therefrom a product comprising conjugated estrogens in which the inorganic salts and proteins present in PMU have been substantially removed. These processes are illustrated in U.S. Pat. Nos. 2,696,265; 2,711,988; 2,834,712; 7,964,586; 5,723,454; 6,855,704; 7081,451; 8,349,819; and 6,855,704, the contents of all of which are incorporated by reference. All of these processed PMU's have a moisture content of less than 2% by weight and is therefore subsumed in the use of the term "dried PMU."

Alternatively, in another embodiment, the present process is applicable to conjugated estrogen products, as identified in the art. These products will also have a moisture content of less than 2% (w/w) and also will be identified herein as dried PMU. These products include the processed PMU's identified hereinabove.

The term w/w, as used herein refers to the weight of a component or compound relative to the total weight of the solid PMU. The term v/v refers to the volume of a compound or component contained in the supercritical fluid extraction vessel relative to the total volume of material. i.e., solid PMU as well as the liquid fluid, in the supercritical fluid extraction vessel.

As used herein, the term alkane refers to an alkyl group containing 1 to 10 carbon atoms. The alkane may be straight-chained or branched or cyclic. In another embodiment, the alkane contains 1 to 6 carbon atoms. Examples of alkanes include methane, ethane, propane, butane, isobutane, sec-butane, tert-butane, pentane, hexane, heptane, octane, nonane and decane. It also includes mixtures of alkanes, such as petroleum ether. The term also includes cycloalkanes, such as cyclohexane, cyclopentane, cycloheptane and the like.

The term alkyl, as used herein in relation to ether, contains 1 to 6 carbon atoms, which may be straight-chained or branched or cyclic. Examples include methyl, ethyl, propyl, isopropyl, butyl, tert-butyl, isobutyl or sec-butyl, pentyl, isopentyl, hexyl, cyclopentyl, or cyclohexyl.

The term aromatic refers to a benzene ring.

As indicated hereinabove, in an embodiment the present application relates to the process of purifying dried PMU using SPE, as described hereinabove. The SFE extraction method employed herein is based on the nonpolar solvent-like behavior of carbon dioxide in the supercritical phase, that is, above the critical point of 31° C. and 72.8 atm (73.80 bar, 1070 psi). This behavior is discussed in Hyatt, "Liquid and Supercritical Carbon Dioxide as Organic Solvents," *J. Org. Chem.*, 1984, 49, 5097-5101. Thus, carbon dioxide behaves as a conventional liquid at high pressure below 31° C., but above the critical point, carbon dioxide is a supercritical fluid. Supercritical carbon dioxide is denser than liquid carbon dioxide, and can effuse through solids like a gas, and dissolve materials like a liquid. As discussed in Hyatt, supercritical carbon dioxide can act as a nonpolar solvent such as a hydrocarbon solvent or methylene chloride. [[See also http://appliedseparations.com/Supercritical/Supercritical_CO2.asp.]]

It was discovered that conjugated estrogens are not soluble in supercritical carbon dioxide, but many impurities occurring in PMU are soluble. Thus, supercritical fluid extraction of a dried mass of PMU has been shown to result in conjugated estrogens with a superior purity profiles as compared to conventional methods of isolating conjugated estrogens from PMU.

The solids of dried PMU's are placed in a supercritical fluid extraction vessel. In an embodiment, the supercritical fluid extraction vessel is comprised of stainless steel, (or any alloy high in Nickel content such as MONEL®) or it may be lined with Teflon. Supercritical carbon dioxide, which is a liquid, is the eluting solvent in the supercritical fluid extraction vessel and is mixed with the solids. In an embodiment, the supercritical carbon dioxide is pumped into the supercritical fluid extraction vessel containing the dried PMU. The supercritical fluid extraction process is conducted at a temperature ranging from about 31° C. to about 40° C. at a pressure ranging from about 1000 psi to about 6000 psi. The supercritical extraction is conducted for a time sufficient to substantially remove the lipophilic impurities. By substantially, it is meant that the resulting product, the conjugated estrogen, contains 10% by weight or less of lipophilic impurity. Temperature control at this stage is critical. At temperatures of less than 31° C., carbon dioxide is not a supercritical fluid, and will lose many of the desirable characteristics of a supercritical fluid, in particular, the ability to act as a non-polar solvent. Temperatures exceeding 40° C. are associated with rapid decomposition of conjugated estrogens. Thus, temperatures at the lower limit of supercriticality are most desirable. In an embodiment, the temperature during the SFE process ranges from about 31° C. to about 35° C., and in another embodiment, the temperature is about 32° C. In an embodiment, the pressure of the carbon dioxide during the supercritical fluid extraction step ranges from about 1100 psi to about 6000 psi, and in another embodiment, from about 2000 psi to about 5000 psi, and in still further embodiment, from about 3000 psi to about 4500 psi, in another embodiment, the pressure is about 4000 psi. In an embodiment, the resulting solids are placed in the supercritical fluid extraction vessel and treated with supercritical carbon dioxide as the liquid phase at about 32° C. and about 4,000 psi. In another embodiment, it is conducted at about 32° C. and about 4,000 psi for about one to about four hours.

The SFE extraction is conducted for sufficient time to separate the conjugated estrogens from substantially all of the steroids present. In an embodiment, this extraction step is conducted for about 30 minutes to about four hours. The extraction is monitored with a UV detector, refractive index detector, scattered light detector, or similar detector such as would be used in liquid chromatography, to monitor the presence of non-polar impurities in the collected carbon dioxide. Such impurities typically include phenolic components, flavonoids, terpenoids, and free (non-conjugated) steroids. The use of the term "lipophilic impurities" and "non-polar impurities" are used interchangeably herein and refer to the phenolic components, flavonoids, terpenoids and free non-conjugated steroids. The present process removes substantially all of these impurities. A key feature of the inventive process is that the conjugated steroids are not dissolved and extracted in the supercritical carbon dioxide. The extraction is complete when no additional non-polar impurities are seen in the effluent from the extraction vessel. Thus, a particular advantage of the instant process is that the extraction can be monitored and stopped when complete.

In an embodiment, a second SFE stage is employed, where water is added to the supercritical carbon dioxide and the solids present in the supercritical fluid extraction vessel. The amount of water added is based on the volume of the material in the extraction vessel. The amount of water added is small such that the moisture content of the material inside the supercritical fluid extraction vessel is about 3% (w/w) or less of the total volume of the solids and the fluid liquid inside the supercritical fluid extraction vessel. But, sufficient water is added so that the pH of the material inside the supercritical fluid extraction vessel ranges from about 4 to about 6. In an embodiment, the amount of water added ranges from about 0.25% to about 3% (v/v). In another embodiment, the amount of water added ranges from about 0.5% to about 1.5% (v/v) and in another embodiment, about 1% of water (v/v) is added. Without wishing to be bound, it is believed that the water reacts with non-polar impurities remaining in and associated with the solids present in the supercritical fluid extraction vessel and forms acids. The acid formed with the addition of water further facilitates the separation of the conjugated estrogens from the lipophilic impurities and enhances the stability of the conjugated estrogens obtained by facilitating the breakdown of any unstable conjugated estrogen that may be present.

When the pH is within the range indicated hereinabove, the non-polar or water immiscible solvent, as defined herein, is then added to the supercritical fluid extraction vessel. The non-polar or water-immiscible solvent may be an alkane, as defined herein. The alkane is unsubstituted, in an embodiment. In another embodiment, the non-polar or water immiscible solvent is benzene, which may be unsubstituted, or substituted with one or two carbon atoms, such as in toluene or xylene. In a further embodiment, the non-polar or water immiscible solvent is R1OR2, wherein R1 and R2 are as defined hereinabove, Thus, R1 may be methyl, ethyl, propyl, isopropyl, butyl, sec-butyl, isobutyl or tert-butyl and R2 may independently be methyl, ethyl, propyl, isopropyl, butyl, sec-butyl, isobutyl or tert-butyl. Examples of non-polar or water immiscible solvent include methane, ethane, propane, benzene, toluene, o-xylene, m-xylene, p-xylene, dimethyl ether, diethyl ether, methyl ethyl ether tert-butyl methyl ether, and the like. The conditions for this step are about the same as for the first SFE stage. In an embodiment, it is conducted at about 32° C. and about 4000 psi. This step is conducted for a time sufficient to remove substantially all of the remaining lipophilic impurities, as with the first SPE stage, the SFE is monitored with a UV detector, refractive index detector, scattered light detector, or similar detector such as would be used in liquid chromatography, to monitor the presence of non-polar impurities in the collected mixture of the liquid carbon dioxide and non-polar and/or water immiscible solvent. The extraction is complete when no additional non-polar impurities are seen in the effluent from the extraction vessel.

The amount of the added non-polar and/or water immiscible solvent ranges from about 0.10% to about 25% (v/v). In an embodiment, the amount of non-polar and/or water immiscible solvent added ranges from about 1% to about 15% (v/v) and in another embodiment, the amount of non-polar and/or water immiscible solvent added ranges from about 7% to about 10% (v/v).

The added non-polar and/or water immiscible solvent increases the lipophilicity of the supercritical fluid, improving the efficiency of extraction of undesired non-conjugated components in the solids. It is run for sufficiently less time than the first SFE stage. In an embodiment, it is conducted for about 5 to about 30 minutes.

When no additional non-polar impurities are seen in the effluent from the extraction vessel, the process is stopped, and the solid material remaining is the purified conjugated estrogens. The solid material is removed from the supercritical fluid extraction vessel.

Undesired lipophilic components can be found in the collection vessels during the SFE. The desired pharmaceutical grade solids are collected from the extraction vessel.

The conjugated estrogens so obtained meet FDA sameness guidelines for conjugated estrogens contained in PREMARIN® tablets.

The conjugated estrogens obtained by the process set forth herein may be formulated into conventional tablets, capsules, and topical delivery formulations, such as creams, ointments, or emulsions. The formulations so obtained are expected to be bioequivalent according to FDA standards to PREMARIN® tablets and topical cream.

As an example of obtaining conjugated estrogens from PMU. The following is exemplary. However, the present invention is not to be considered limited to this method.

The PMU employed in this embodiment is obtained from pregnant mares in cold weather climates. The animals are bred during the spring or summer months, and urine is collected from the pregnant mares during cold weather months from November to March. These are periods in cold weather climates when the outdoor temperature is reliably below about 10° C. At warmer air temperatures, the conjugated estrogens rapidly decompose.

In one embodiment, raw PMU collected over a range of months from a group of pregnant mares is collected is processed as described herein, and blended to provide an optimal blend of estrogens.

In the processing of PMU, freshly collected unprocessed PMU may be allowed to settle for sufficient time to separate suspended solids. In an embodiment, this may take about 24 to about 48 hours at a temperature ranging from about 2° C. to about 10° C. prior to the next steps, to separate suspended solids. The supernatant is then carefully pumped off.

The PMU is dried by conventional methods known in the art such that the moisture content is less than 2% by weight. The PMU is subjected to a temperature and pressure to reduce the moisture content to less than 2% by weight. In an embodiment, the PMU are subjected to temperature of about 40° C. or less and at a pressure of less than 2 torr (e.g., less than about 1 torr) for sufficient time to reduce the moisture content to the above-level. In another embodiment, it may be spray dried or lyophilized. In another embodiment the PMU solution is dried in a rotary evaporator at low temperature and high vacuum. The temperature at this step ranges from about 15° C. to about 30° C., and the vacuum pressure is about 0.25 mm Hg or less. It is important to maintain the material at less than 40° C. at all times to minimize decomposition.

Each of the following steps until the supercrtitical fluid extraction step is optional. In other words, the dried PMU may be subjected to SPE or it may be further treated by any one and a combination of one or more of the following steps in any particular order.

Optionally, the raw PMU is filtered to begin removing impurities. In an embodiment, the PMU is filtered by ultra filtration through one or a series of successively finer membranes, for example, with nominal molecular weight limits (NMWL) of 1000 kilo Dalton, 300 kilo Dalton, 100 kilo Dalton, 30 kilo Dalton, 10 kilo Dalton, 8 kilo Dalton, or 5 kilo Dalton, or some combination of these or similar pore sizes. In an embodiment, 100 kilo Dalton, 10 kilo Dalton, and 5 kilo Dalton membranes are employed in successive steps. Preferably, the final stage is the 5 kilo Dalton membrane. At this stage, components with a molecular weight of greater than about 5000 Daltons are removed from the resulting liquid, such as proteins, bacteria, and viruses. The filtrate from this ultra filtration step is employed in later steps in the inventive process. In an embodiment, the PMU supernatant from the settling step is treated by this ultra filtration step.

In an embodiment, the PMU, which optionally was allowed to settle for 24 to 48 hours as described above, and optionally is treated by ultra filtration to remove components with a molecular weight of greater than about 5000 Daltons, is treated with nanofiltration to remove components with a molecular weight of less than about 250 Daltons. Both Dow NF90 and Dow NF270 membranes or similar nanofiltration membranes can be employed. The retentate from this process is retained.

By the above ultrafiltration and nanofiltration steps, a mass of PMU will be obtained in which all dissolved components (solutes) range from about 250 to about 5000 Daltons.

Each of the filtration stages, if employed, reduces the volume of the liquid containing conjugated estrogens. At the completion of the ultrafiltration and nanofiltration stages, the volume of liquid may be reduced to about 7% to about 10% of the starting volume of PMU.

In an optional embodiment, the PMU subjected to sequential ultrafiltration and nanofiltration is treated with activated charcoal, which can remove colored impurities and lactone impurities.

The PMU dried at this stage may optionally have been treated with all or some combination of the settling, ultrafiltration, nanofiltration, and activated charcoal steps described above.

The resulting solids are placed in the supercritical fluid extraction vessel, and treated with supercritical carbon dioxide as described hereinabove, and the desired pharmaceutical grade solids are collected from the supercritical fluid extraction vessel.

The material obtained from this process described herein is obtained in good yields, and is expected to have a conjugated estrogen content ranging from about 30% to about 40% by weight, and about 0.5% by weight free steroids or less. This level of purity is novel compared to known processes for purifying conjugated estrogens from PMU. Thus, conjugated estrogens with an assay of 35% or higher or 40% or higher, with 0.3% or less of free steroids may be obtained the instant process.

The conjugated estrogens so obtained meet FDA sameness guidelines for conjugated estrogens contained in PREMARIN® tablets.

The conjugated estrogens obtained by the process set forth herein may be formulated into conventional tablets, capsules, and topical delivery formulations, such as creams, ointments, or emulsions. The formulations so obtained are expected to be bioequivalent according to FDA standards to PREMARIN® tablets and topical cream.

In an embodiment, conjugated estrogens from different collection periods (November to March) are purified by this process and blended, because some of the desired conjugated estrogens are secreted earlier in the pregnancy, such as estrone sulfate, and other estrogenic components occur later in the pregnancy, such as equilin sulfate. Thus, optimal blends contain conjugated estrogens from the full season.

The following non-limiting example further exemplifies the teachings of the present disclosure.

EXAMPLE

Twenty-five gallons (95 L) of pregnant mare's urine (PMU), with a conjugated estrogen content of 0.4 g per gallon was obtained from a herd of pregnant mares, collected in March, and maintained at freezing temperatures or a maximum of 10° C. prior to processing.

This mass of PMU was warmed to above freezing and allowed to settle for 24 hours at 5-10° C., and the supernatant was carefully pumped off without disturbing the precipitated solids.

The resulting volume of PMU was filtered through three successively smaller ultrafiltration membranes, with NMWL cutoffs of 100 kiloDaltons, 10 kiloDaltons, and 5 kiloDaltons. The filtrate of each ultrafiltration step was used for the next step. Thus, following the final ultrafiltration membrane, any dissolved components with a mass greater than 5000 Daltons was removed.

The resulting mass of PMU was next passed through a Dow NF90 nanofiltration membrane, and the retentate was collected. The step removed dissolved components with a MW of less than, and up to about 250 Daltons. The volume of the PMU at this point was about 6.75 L. This liquid was passed through a bed of activated charcoal.

The resulting material was dried in a rotary evaporator at low temperature, preferably not exceeding 15° C., and high vacuum, sufficient to vaporize the water therein, for example, at 0.1 mm Hg or less.

The resulting solids were placed in a supercritical fluid extraction vessel and treated with supercritical carbon dioxide with UV monitoring at 254 nm. When no additional impurities were eluted, the extraction was stopped. The total time in the SFE vessel exposed to supercritical carbon dioxide was about 1.5 hours.

Pharmaceutical grade conjugated estrogens were then collected from the SFE vessel. Yield was 22.6 g (79.9% of theoretical). The conjugated estrogen assay was 35%. Free steroid content was 0.3%.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. A method for preparing purified conjugated estrogens comprising subjecting a mass of pregnant's mare urine which has been dried to a moisture content of less than 2% by weight to supercritical fluid extraction ("SFE") in a supercritical fluid extraction vessel using supercritical carbon dioxide as the fluid phase to remove impurities present therein and isolating purified conjugated estrogens therefrom.

2. The method of claim 1, wherein the supercritical carbon dioxide is employed at a temperature of about 31° C. to about 35° C. as measured in the supercritical fluid extraction vessel and a pressure of about 1100 psi to about 6000 psi.

3. The method of claim 1, wherein the supercritical carbon dioxide is employed at a temperature of about 32° C. as measured in the supercritical fluid extraction vessel and a pressure of about 2000 to about 4500 psi.

4. The method of claim 1, in which prior to obtaining the dried mass of pregnant mare's urine, the mass of pregnant mares' urine is placed in a vessel and allowed to settle for about 24 hours to about 48 hours at a temperature of about 2° C. to about 10° C., and the supernatant is drawn off from said tank, wherein said supernatant contains dissolved conjugated estrogens.

5. The method of claim 1, in which prior to obtaining the dried mass of pregnant mare's urine, the mass of pregnant mares' urine is filtered through one or more ultrafiltration membranes with a NMWL cutoff selected from 1000 kiloDaltons, 300 kiloDaltons, 100 kiloDaltons, 30 kiloDaltons, 10 kiloDaltons, 8 kiloDaltons, or 5 kiloDaltons, or a combination thereof, and the filtrate from each ultrafiltration step is collected, wherein at least the last or only ultrafiltration membrane has a NMWL cutoff of 5 kiloDaltons, prior to drying and supercritical fluid extraction.

6. The method of claim 1, in which prior to obtaining the dried mass of pregnant mare's urine, the mass of pregnant mare's urine is passed through a nanofilter, with a pore size allowing dissolved components of 250 Daltons or less to pass through, and the retentate of said nanofiltration is collected, prior to drying and supercritical fluid extraction.

7. The method of claim 1, in which the carbon dioxide downstream from the supercritical fluid extraction vessel is monitored with a detector selected from a UV detector, a refractive index detector, and a scattered light detector.

8. A method of isolated conjugated estrogens from a mass of pregnant mares' urine (PMU), comprising
 a. placing said mass of PMU in a vessel and allowing said mass to settle for about 24 hours to about 48 hours at a temperature of about 2° C. to about 10° C., and drawing off the supernatant from said tank, wherein said supernatant contains dissolved conjugated estrogens;
 b. filtering the resulting supernatant through one or more ultrafiltration membranes with a NMWL cutoff selected from 1000 kiloDaltons, 300 kiloDaltons, 100 kiloDaltons, 30 kiloDaltons, 10 kiloDaltons, 8 kiloDaltons, or 5 kiloDaltons, or a combination thereof, and collecting the filtrate from each ultrafiltration step, wherein at least the last or only ultrafiltration membrane has a NMWL cutoff of 5 kiloDaltons;
 c. passing the resulting filtrate through a nanofilter with a pore size allowing dissolved components of 250 Daltons or less to pass through, and collecting the retentate of said nanofiltration;
 d. optionally filtering the said retentate through a bed of activated charcoal;
 e. drying the resulting liquid in a rotary evaporator apparatus at a temperature of about 30° C. or less and a vacuum of about 0.25 mm Hg or less to provide a dried solid;
 f. placing said dried solid in a supercritical fluid extraction vessel and performing a supercritical fluid extraction of said dried solid with supercritical carbon dioxide maintained at a temperature of about 31° C. to about 35° C. as measured in the supercritical fluid extraction vessel and a pressure of about 1100 psi to about 6000 psi;
 g. monitoring said supercritical fluid extraction with a UV detector, refractive index detector, or scattered light detector in the downstream effluent of the extraction vessel, and ending said supercritical fluid extraction when the effluent is substantially free of impurities; and
 h. collecting the purified conjugated estrogen solids from the extraction vessel.

9. The method of claim 1 which additionally comprises adding water to the supercritical liquid carbon dioxide in the supercritical fluid extraction vessel containing the mass of pregnant's mare urine that had been subjected to a first supercritical fluid extraction using supercritical carbon dioxide as the fluid phase extraction to change the pH of the liquid to about 4 to about 6 and then adding a non-polar or water immiscible solvent to the supercritical carbon dioxide and water mixture and subjecting said mass of pregnant mare's urine to supercritical fluid extraction using the mixture of supercritical carbon dioxide, water and the non-polar or water immiscible solvent as the fluid phase extraction.

10. The method claim 9 wherein the amount of water added is about 0.25% to about 3% (v/v).

11. The method of claim 9 wherein the non-polar or water immiscible solvent is present in about 0.10% to about 25% (v/v).

12. The method of claim 9 wherein the non-polar or water immiscible solvent is methane, ethane, propane, hexane, benzene, tert-butyl methyl ether.

13. The method of claim 8 wherein the product of step h is subjected to a second supercritical fluid extraction in a supercritical fluid extraction vessel using supercritical carbon dioxide in mixture with water and a non-polar or water immiscible solvent as the fluid phase to remove non-polar impurities.

14. The method of claim 13 wherein the amount of water is about 0.25% to about 3% (v/v).

15. The method of claim 13 wherein the non-polar or water immiscible solvent is present in about 0.10% to about 25% (v/v).

16. The method of claim 13 wherein the non-polar or water immiscible solvent is methane, ethane, propane, hexane, benzene, tert-butyl methyl ether.

17. The method of claim 13 wherein the mixture of water and supercritical carbon dioxide is acidified to a pH of about 4 to about 6 prior to the addition of the non-polar or water immiscible solvent.

\* \* \* \* \*